United States Patent [19]  
Tschopp et al.

[11] Patent Number: 4,680,266  
[45] Date of Patent: Jul. 14, 1987

[54] CELL CULTURE CHAMBER WITH MEANS FOR AUTOMATIC REPLENISHMENT OF NUTRIENT

[75] Inventors: Alexander Tschopp, Zürich, Switzerland; Claudy-Gabrielle Gruenblat-Nordau, Paris, France; Beat Huber, Hombrechtikon; Augusto Cogoli, Zürich, both of Switzerland

[73] Assignee: Contraves AG, Zürich, Switzerland

[21] Appl. No.: 800,583

[22] Filed: Nov. 21, 1985

[51] Int. Cl.[4] .............................................. C12M 3/00
[52] U.S. Cl. ................................... 435/284; 435/287; 604/892
[58] Field of Search .............................. 435/284–287, 435/311; 604/892

[56] References Cited

U.S. PATENT DOCUMENTS

| | | | |
|---|---|---|---|
| 3,677,337 | 7/1972 | Midolo | 165/104.22 |
| 3,845,770 | 11/1974 | Theeuwes et al. | 604/893 |
| 3,887,436 | 6/1975 | Haddad et al. | 435/285 |
| 4,193,398 | 3/1980 | Refson | 417/48 X |
| 4,208,483 | 6/1980 | Lee | 435/284 |
| 4,435,508 | 3/1984 | Gabridge | 435/284 |
| 4,546,086 | 10/1985 | Hounsell | 435/287 |

Primary Examiner—Samuel Scott  
Assistant Examiner—Allen J. Flanigan  
Attorney, Agent, or Firm—Werner W. Kleeman

[57] ABSTRACT

The apparatus which includes a cell culture chamber enables cell biological experiments with botanical, zoological or homological cells to be carried out. The apparatus comprises a pump housing and a cell culture block with a cell culture chamber therein in which the cell culture medium or nutrient can be automatically and continually exchanged by the action of an osmotic fluid pump connected to the chamber. The osmotic fluid pump is activated by a fluid filled into a cavity in the pump housing. The osmotic fluid pump forces its precharged contents, i.e. the cell culture medium or nutrient, through an inlet passage into the cell culture chamber. The exhausted or expanded cell culture medium or nutrient can drain or exhaust through an outlet passage into the cavity of the pump housing. This ensures that no excess pressures arise in the system. The apparatus is especially well-suited for carrying out or implementing biological experiments under zero gravity conditions such as prevail in spaceships. The process transpires automatically and without supplementary intervention by astronauts. Even in terrestrial laboratories, the apparatus is especially well-suited for carrying out or performing experiments in the areas of developmental biology and embriology, since nutrients or other substances must often be continuously supplied in these fields.

2 Claims, 2 Drawing Figures

CELL CULTURE CHAMBER WITH MEANS FOR AUTOMATIC REPLENISHMENT OF NUTRIENT

BACKGROUND OF THE INVENTION

The present invention broadly relates to cell culture chambers and, more specifically, pertains to a new and improved construction of an apparatus for carrying out cell-biological experiments.

In its more particular aspects, the present invention relates to an apparatus for carrying out or performing cell-biological experiments on or with botanical, zoological or homological cells. A nutrient or nutrient medium can be continually replaced by the action of an osmotic fluid pump. The apparatus constitutes a sealed system, which, once set in operation, operates or runs fully automatically and without additional energy requirements.

Cell culturing technology, external to organisms, has been a widespread method in scientific laboratories and in industry since approximately 1950. Botanical, zoological or homological cells are caused to multiply in a nutrient medium within special containers. After a cell cycle, i.e. after the cell count has doubled, the nutrient medium is normally expended or exhausted and must be replaced by a fresh nutrient medium. This presents no particular problems in a normally equipped cell-biological laboratory.

Since 1981, when the American space ferry, "Space Shuttle", was introduced, a new problem has arisen: the fact that cell-biological experiments can now be carried out under zero gravity conditions inevitably led to the development of new laboratory methods. It is not easy to handle or manage fluids under zero gravity conditions, since fluids cannot readily be poured or transferred from one container to the other. It is furthermore desirable, for various reasons, to develop techniques that require the least possible amount of intervention by accompanying astronauts.

SUMMARY OF THE INVENTION

Therefore, with the foregoing in mind, it is a primary object of the present invention to provide a new and improved construction of an apparatus for carrying out cell-biological experiments which does not exhibit the aforementioned drawbacks and shortcomings of prior art constructions.

Another and more specific object of the present invention aims at providing a new and improved construction of an apparatus for carrying out cell-biological experiments of the previously mentioned type in which a desired cell culture medium or nutrient medium is replaced or replenished automatically without requiring human intervention.

Yet a further significant object of the present invention aims at providing a new and improved construction of an apparatus of the character described for carrying out cell-biological experiments and which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds, the apparatus of the present invention is manifested by the features that it comprises a cell culture chamber having an inlet passage and an outlet passage and an osmotic fluid pump connected to the inlet passage for continuously dispensing a desired cell culture medium or nutrient to the cell culture chamber. The outlet passage serves for removal of expended cell culture medium.

The osmotic fluid pump used in this system was originally developed for other purposes: when placed under the skin or in a body cavity of a living creature or entities, the osmotic fluid pump can release accurately dosed or measured liquids, e.g. medicaments or medications, over an extended period. These pumps are commercially available with various specifications.

The range of application of the proposed apparatus is not limited to the space laboratory. Even in terrestrial developmental biology and embriology studies, the problem of continuously supplying nutrient medium and other fluid substances also arises. Here, too, the present invention can be employed to advantage.

In all cell-biological experiments, it is important to be able to work under absolutely sterile conditions. For this reason, the apparatus of the present invention employs only materials which can be heat or temperature sterilized, e.g. in an autoclave.

Since cell cultures are generally sensitive to pressure, excess pressure should not be allowed to build up in a sealed or closed system. The apparatus of the present invention ensures that none will.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally used the same reference characters to denote the same or analogous components and wherein.

DETAILED DESCRIPTION OF THE PREFERRED EMBODIMENTS

Figure 1:
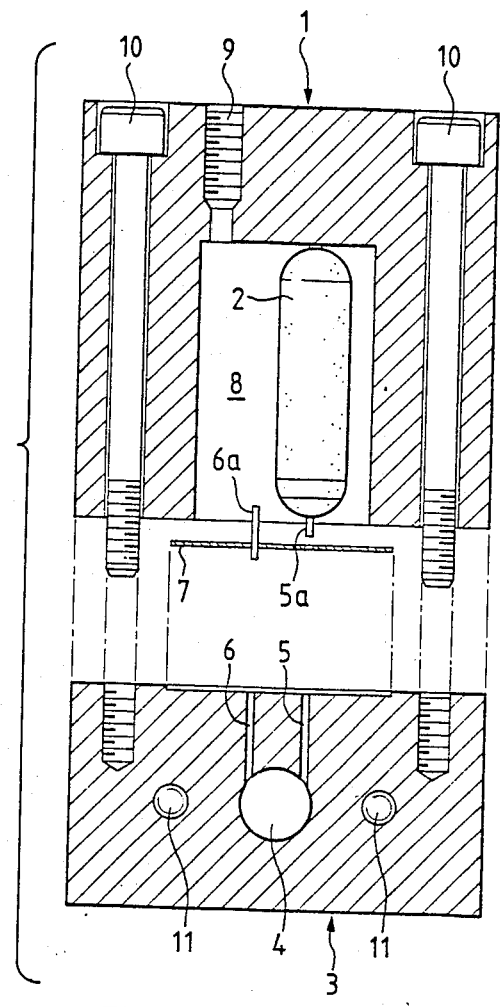
FIG. 1 schematically shows an exemplary embodiment of an apparatus comprising a pump housing cavity as well as a cell culture block for replenishing a nutrient automatically in a cell culture chamber in cross-section and dismantled state.

Describing now the drawings, it is to be understood that to simplify the showing thereof only enough of the structure of the apparatus for carrying out cell-biological experiments has been illustrated therein as is needed to enable one skilled in the art to readily understand the underlying principles and concepts of this invention. Turning now specifically to FIG. 1 of the drawings, the apparatus illustrated therein by way of example and not limitation will be seen to essentially comprise two major functional components. One major component is a pump housing 1 with a built-in or integrated osmotic fluid pump 2. The other major component is a cell culture block 3 which is equipped with or features a cell culture chamber 4. The cell culture chamber 4 has or comprises an inlet passage 5 and an outlet passage 6 in the assembled condition; i.e., when the pump housing 1 and the cell culture block 3 are assembled together. An outlet opening 5a of the osmotic fluid pump 2 is connected with the inlet passage 5 and a return or drain connection 6a is connected with the outlet passage 6.

This return or drain connection 6a can optionally be equipped with a one-way valve which is not illustrated. In order to properly seal the outlet opening 5a from the return or drain connection 6a, both the outlet opening 5a and the return or drain connection 6a penetrate or extend through a silicon membrane 7. After fastening the pump housing 1 to the cell culture block 3, for instance by means of screws or bolts 10, the silicon membrane 7 is fixed in a not particularly referenced shallow rectangular groove or cavity where it acts as a seal or gasket.

The cell culture chamber 4 is filled as follows: after a first sight glass 12 has been secured by a bezel 13 with the aid of screws 11, the cell culture can be poured or introduced into the cell culture chamber 4. After the cell culture has been poured or introduced into the cell culture chamber 4, the cell culture chamber 4 can be sealed by a second sight glass 12, a second bezel 13 and screws 11 or equivalent structure. A further opening or filler opening or port 9 is provided in the pump housing 1 which is connected with a pump housing cavity 8. The further opening or port 9 can be sealed by a screw plug which is not illustrated. In the pump housing cavity 8, a desired fluid medium is introduced which drives the osmotic fluid pump 2. This fluid sets the system in operation. The fluid medium previously filled into the osmotic fluid pump 2 is then continuously pumped through the outlet opening 5a into the cell culture chamber 4. The action of draining off expended fluid through the return or drain connection 6a in the pump housing cavity 8 prevents the arisal of an overpressure at any location in the system.

Figure 2:
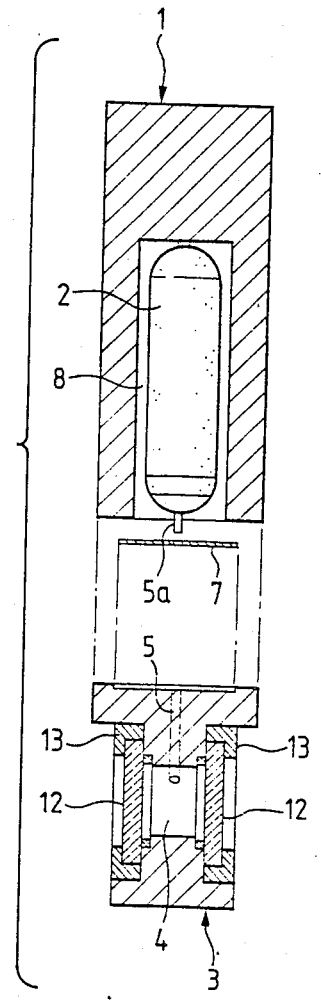
FIG. 2 schematically illustrates a longitudinal section through the apparatus according to FIG. 1, in which the details of a cell culture chamber are to be seen.

The assembly of the apparatus illustrated in FIGS. 1 and 2 in a dismantled condition is substantially effected by motions indicated by the dash-dotted lines. The pump housing 1 and the cell culture block 3 are pressed towards each other by the screws or bolts 10 and so form or constitute a unit.

While there are shown and described present preferred embodiments of the invention, it is to be distinctly understood that the invention is not limited thereto, but may be otherwise variously embodied and practiced within the scope of the following claims. Accordingly,

What we claim is:

1. An apparatus for performing cell-biological experiments, especially under zero gravity conditions, comprising:
    a housing;
    said housing defining a pump cavity, a cell culture chamber, an inlet passage leading from said pump cavity to said cell culture chamber and an outlet passage leading from said cell culture chamber to said pump cavity;
    an osmotic fluid pump located in said pump cavity and connected to said inlet passage for continuously dispensing a desired cell culture medium from said osmotic fluid pump into said cell culture chamber; and
    said outlet passage serving for removal of expended cell culture medium from said cell culture chamber and return of said expended cell culture medium into said pump cavity.

2. The apparatus as defined in claim 1, wherein:
    said apparatus, with the exception of said osmotic fluid pump, comprises a material which can be temperature sterilized.

* * * * *